United States Patent
Mamerski et al.

(10) Patent No.: US 10,028,526 B2
(45) Date of Patent: Jul. 24, 2018

(54) PROTECTIVE MEMBER FOR ROD-LIKE ELEMENTS, IN PARTICULAR ROD SECTIONS AND/OR AN ENDLESS ROD, TRAVELLING WITHIN A MEASURING HEAD USED IN TOBACCO INDUSTRY AND CORRESPONDING MEASURING HEAD

(71) Applicant: International Tobacco Machinery Poland Sp. z o.o., Radom (PL)

(72) Inventors: Marcin Mamerski, Radom (PL); Pawel Gruszka, Bielicha (PL)

(73) Assignee: INTERNATIONAL TOBACCO MACHINERY POLAND SP. Z O.O., Radom (PL)

( * ) Notice: Subject to any disclaimer, the term of this patent is extended or adjusted under 35 U.S.C. 154(b) by 189 days.

(21) Appl. No.: 14/882,696

(22) Filed: Oct. 14, 2015

(65) Prior Publication Data
US 2016/0103076 A1    Apr. 14, 2016

(30) Foreign Application Priority Data
Oct. 14, 2014    (PL) .......................................... 409753

(51) Int. Cl.
*H01J 7/00* (2006.01)
*A24D 3/02* (2006.01)
(Continued)

(52) U.S. Cl.
CPC ............ *A24D 3/025* (2013.01); *A24C 5/3412* (2013.01); *G01N 21/952* (2013.01)

(58) Field of Classification Search
CPC ..................................................... A24C 5/3412
(Continued)

(56) References Cited

U.S. PATENT DOCUMENTS 3,386,578 A    6/1968    Black et al.
4,986,285 A    1/1991    Radzio et al.
(Continued)

FOREIGN PATENT DOCUMENTS

EP    1302117 A1    4/2003
EP    2641487 A2    9/2013
(Continued)

OTHER PUBLICATIONS

European search report for corresponding European application No. 15 18 4999.9-1656, search completed on Mar. 10, 2016.

*Primary Examiner* — Thanh Luu
(74) *Attorney, Agent, or Firm* — Browdy and Neimark, PLLC

(57) ABSTRACT

A protective member for rod-like elements, in particular rod sections and/or an endless rod, travelling within a measuring head used in tobacco industry, the measuring head including at least two neighboring sensor units enabling to take measurements of the parameters of the rod-like elements by the radiation emitted and received by the sensor units, the protective member extending through the operation zones of the specific sensor units. The protective member includes compartments defined therein, each compartment corresponding to the operation zone of one sensor unit and each compartment including at least one first opening enabling percolation of the radiation. A measuring head including the protective member is also disclosed.

9 Claims, 3 Drawing Sheets

Figure 1:
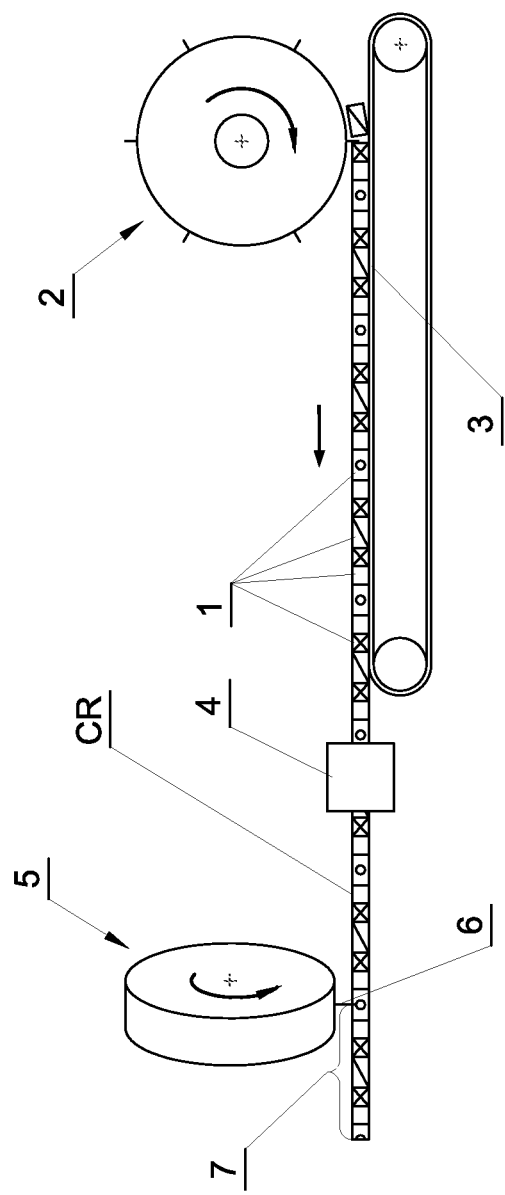

(51) Int. Cl.
*A24C 5/34* (2006.01)
*G01N 21/952* (2006.01)

(58) Field of Classification Search
USPC .................. 131/280–282, 905, 906, 908;
250/559.24–559.26
See application file for complete search history.

(56) References Cited

U.S. PATENT DOCUMENTS

| | | |
|---|---|---|
| 5,675,144 A | 10/1997 | Focke et al. |
| 6,763,838 B2 * | 7/2004 | Suzuki ................ A24C 5/3412 |
| | | 131/280 |
| 2011/0162665 A1 | 7/2011 | Burov et al. |

FOREIGN PATENT DOCUMENTS

| | | |
|---|---|---|
| GB | 1 461 903 | 1/1977 |
| GB | 2 179 444 | 3/1987 |
| GB | 2205028 A | 11/1988 |

* cited by examiner

PROTECTIVE MEMBER FOR ROD-LIKE ELEMENTS, IN PARTICULAR ROD SECTIONS AND/OR AN ENDLESS ROD, TRAVELLING WITHIN A MEASURING HEAD USED IN TOBACCO INDUSTRY AND CORRESPONDING MEASURING HEAD

The invention relates to a protective member for rod-like elements, in particular rod sections and/or an endless rod, travelling within a measuring head used in tobacco industry. The invention also relates to a corresponding measuring head employing the protective member.

Machines for producing filter or cigarette rod sections by cutting a continuous filter or cigarette endless rod are commonly used in tobacco industry. The filter endless rods may be produced from different filter segments or from one kind of a filtering material.

The parameters of the endless rods or rod sections are measured during or upon production. The rods are passed through a measuring head equipped with numerous sensors. A measuring head of a machine for producing multisegment filter rods may be equipped with several kinds of different measuring sensors emitting radiation in order to enable to take measurements of the parameters of the rods passing through the measuring head. Zones of operation of the individual sensors are located very close to each other. In order to increase the precision of the measurements the endless rod should be guided ahead of, behind or through the measuring head.

U.S. Pat. No. 4,986,285 discloses a measuring head employing three sensors arranged radially around a cylindrical hole in which an endless rod is guided.

US 2011/0162665A1 discloses a measuring head having guiding elements at its inlet and outlet, the measuring head being equipped with several sensors the zones of operation of which are not separated.

EP 2641487A2 presents a measuring head including several sensors and a guiding channel for a rod located between the sensors. A replaceable protective sleeve in which the endless rod is guided is located within the channel. The protective sleeve forms a cylindrical longitudinal barrier between a process zone and a measurement zone, the process zone being located within the protective sleeve and forming one common cylindrical space for all the sensors. The aim was to separate the process zone from the measurement zone in order to eliminate infiltration of the impurities (e.g. dust) present in the process zone, impairing the operation of the measuring head.

A disadvantage of the above mentioned state of art solutions consists in that the neighboring radiation emitting sensors may disturb the operation of each other.

In view of the above, it is an object of the current invention to provide a protective member for the rod-like elements transported in a measuring head of the above described type, enabling to separate the operation zones of the specific sensors from each other.

It is also an object of the present invention to provide a measuring head in which the operation zones of the specific sensors are separated from each other.

It is also an object of the present invention to provide a measuring head ensuring improved precision of measurements compared to the state of art.

According to the invention a protective member is provided for rod-like elements, in particular rod sections and/or an endless rod, travelling within a measuring head employed in tobacco industry, the measuring head comprising at least two neighboring sensor units enabling to take measurements of the parameters of said rod-like elements by means of the radiation emitted and received by said sensor units, the protective member extending through the operation zones of the individual sensor units.

The protective member according to the invention is characterized by comprising compartments defined therein, each compartment corresponding to the operation zone of one sensor unit and each compartment comprising at least one first opening enabling percolation of said radiation.

Preferably, the protective member has a generally tubular shape and separate compartments are defined by means of flanges, each flange delimitating, together with a rod-like element travelling within the protective member, a space assigned to each sensor unit, said space being located between the peripheral wall of the rod-like element, by two neighboring flanges and by the internal wall of the protective member, and said space being substantially inaccessible to the radiation emitted by the neighboring sensor units.

Preferably, each compartment further comprises at least one second opening enabling percolation of said radiation, located opposite to a corresponding first opening, each sensor unit comprising a radiation source located on one side of the protective member and a radiation receiver located on the opposite side of the protective member opposite to the respective radiation source.

The protective member is preferably made of a material radiopaque to the radiation emitted and received by the sensor units, the radiation being selected from a group comprising visible radiation, infrared radiation and ultraviolet radiation.

According to the invention a measuring head is provided for use in tobacco industry, the measuring head comprising at least two neighboring sensor units enabling to take measurements of the parameters of rod-like elements, in particular rod sections and/or an endless rod, travelling within the measuring head, by means of radiation emitted and received by the sensor units, the measuring head comprising a protective member for the rod-like elements extending through the operation zones of the specific sensor units.

The measuring head according to the invention is characterized in that compartments are defined in the protective member, each compartment corresponding to the operation zone of one sensor unit and each compartment comprising at least one first opening enabling percolation of said radiation.

Preferably, the measuring head has a protective member having a generally tubular shape and separate compartments are defined by means of flanges, each flange delimitating, together with the rod-like element travelling within the protective member, a space being assigned to each sensor unit, said space being located between the peripheral wall of the rod-like element, by two neighboring flanges and by the internal wall of the protective member, and said space being substantially inaccessible to the radiation emitted by the neighboring sensor units.

Preferably, each sensor unit comprises a radiation source and a radiation receiver, both being located on the same side of the protective member.

Alternatively, each sensor unit comprises a radiation source located on one side of the protective member and a radiation receiver located on the opposite side of the protective member opposite to the respective radiation source, each compartment of the protective member further comprising at least one second opening enabling percolation of said radiation, located opposite to a corresponding first opening.

Preferably, the protective member of the measuring head is made of a material radiopaque to the radiation emitted and received by the sensor units, the radiation being selected from a group comprising visible radiation, infrared radiation and ultraviolet radiation.

Experiments performed using a measuring head according to the invention comprising the protective member according to the invention have shown that the operation zones of the neighboring sensor units are effectively separated from each other and no radiation interference occurs. Consequently, the precision of the measurements is very high. It has also turned out that although impurities in the form of fine particles of a filtering or wrapping material tend to accumulate on the peripheries of the compartments of the protective member, this effect does not disturb the measurements and consequently the time between necessary replacements of the protective member may be prolonged.

Figure 2:
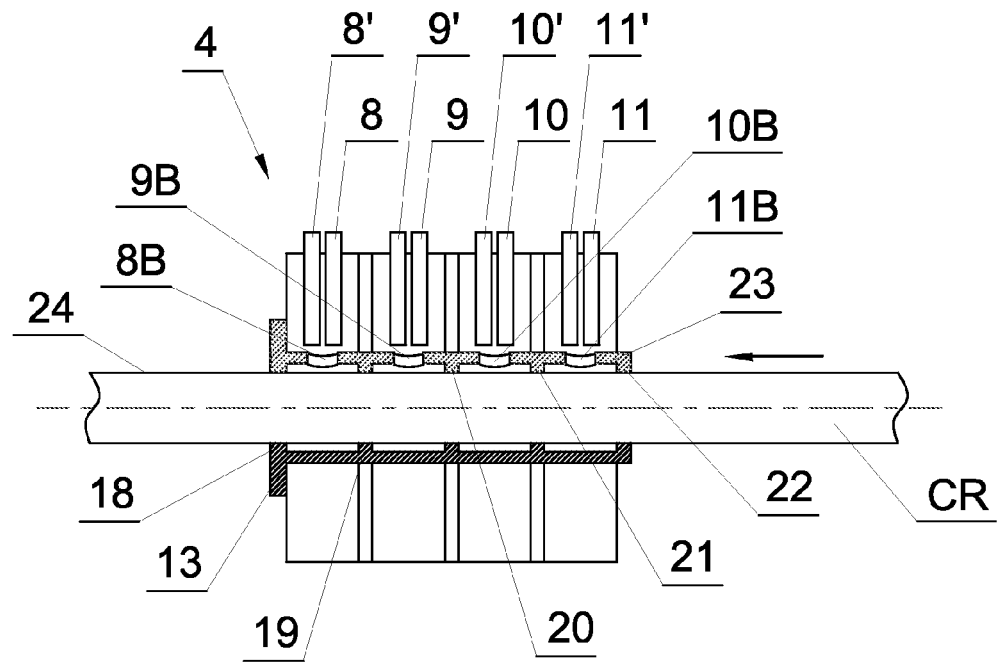
Figure 3:
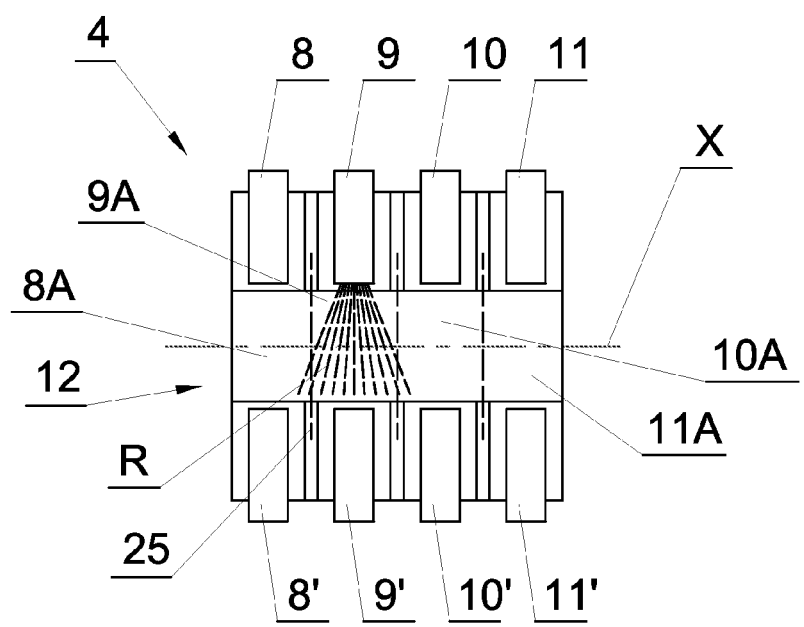
Figure 4:
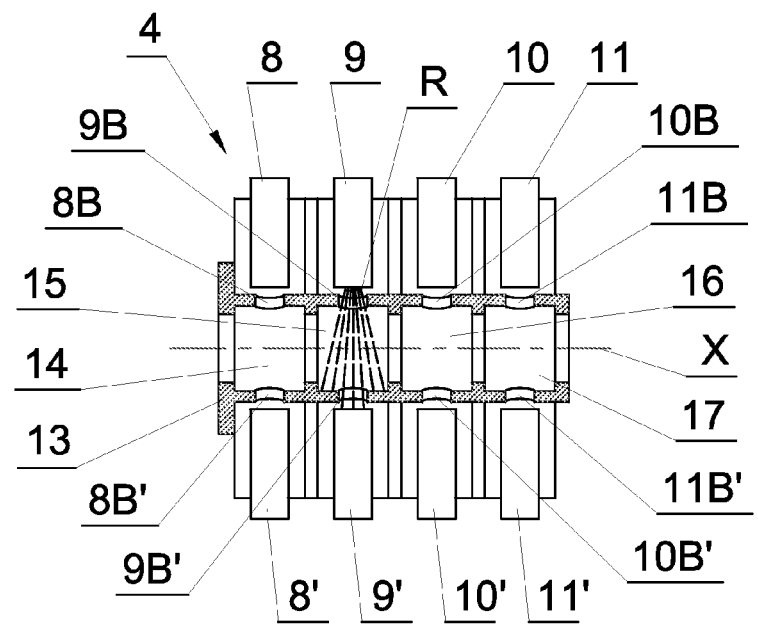
Figure 5:
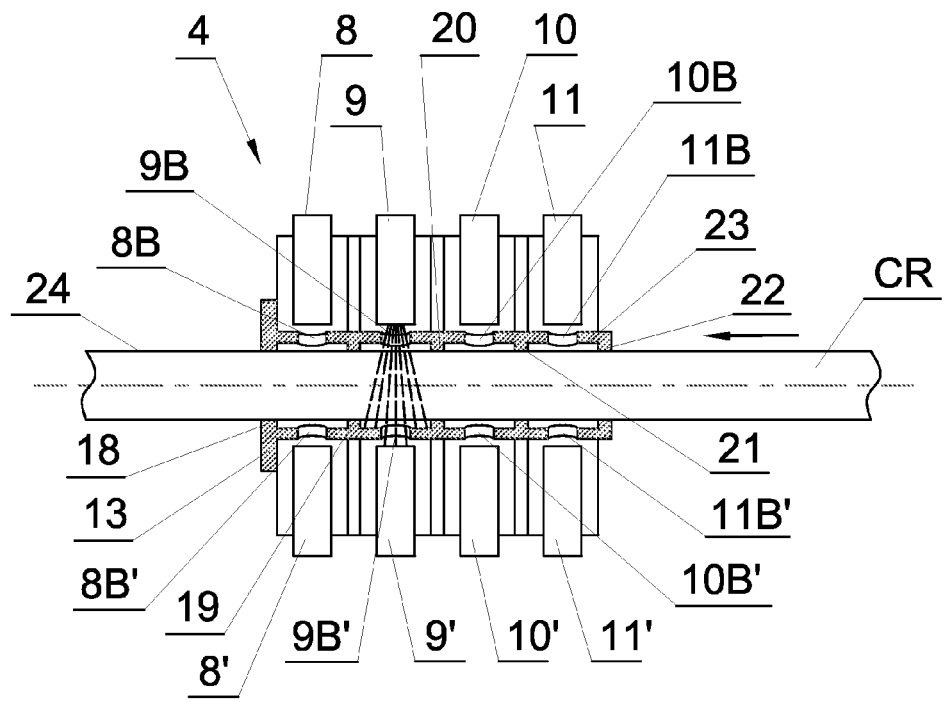

Preferred embodiments of the invention have been further described with reference to the appended drawing in which:

FIG. 1 schematically shows a fragment of an exemplary machine used in tobacco industry;

FIG. 2 schematically shows a longitudinal section of the measuring head with the protective member according to a first embodiment in which a rod-like element is transported;

FIG. 3 schematically shows a longitudinal section of the measuring head according to the invention in which the protective member is not present;

FIG. 4 schematically shows a longitudinal section of the measuring head with the protective member according to a second embodiment, in which the rod-like element is not present;

FIG. 5 schematically shows a longitudinal section of the measuring head of FIG. 4 in which a rod-like element is present.

In a machine shown in FIG. 1, for producing rod-like elements having a form of multisegment rod sections, the segments 1 are delivered to a conveyor 3 by means of a feeding device 2. The segments 1 travel in a direction shown by an arrow while being wrapped in a wrapping material (not shown). An endless multisegment rod CR is formed as a result of the process of wrapping; it proceeds to pass through a measuring head 4. Then the multisegment rod sections having a length 7 are cut from an endless rod by means of a cutting head 5 equipped with knives 6.

The present invention may be used in production of any type of final or semi-finished products of tobacco industry, e.g. the multisegment filter rod sections containing filter segments, the multisegment filter rod sections containing filter segments and additional components for modifying or imparting aroma, the multisegment filter rod sections containing filter segments and additional objects for modifying filtering proprieties of the used materials, the multisegment filter rod sections containing both filter segments and non-filter segments, the multisegment articles having a lowered tobacco content, as well as to the cigarettes with an appended single or multi segment mouthpiece.

The measuring head 4 according to the first embodiment of the invention is shown in FIG. 2 The measuring head 4 is adapted to take measurements of the parameters of an endless rod CR transported in the machine. The measuring head 4 is equipped with four sensor units 8-8', 9-9', 10-10', 11-11', each of which comprises a radiation source 8, 9, 10, 11 and a radiation receiver 8', 9', 10', 11'. The radiation source and the radiation receiver of each sensor unit are located on the same side of a through channel 12 inside which the rod-like elements are guided.

In FIGS. 2-5, four sensor units 8-8', 9-9', 10-10', 11-11' are shown for the sake of simplicity as if they were angularly aligned with respect to an axis X of the measuring head 4. In practice, any number of sensor units may be used and they may be offset by any angle with respect to the axis X. Further, the radiation sources and a radiation receivers as such may be spaced from the measuring head according to the invention, whereas their measuring contacts, e.g. the photosensitive end pieces of the optical sensors, are associated with the measuring head. The sensor units 8-8', 9-9', 10-10', 11-11' of the measuring head according to the invention are selected from typical sensors employed in tobacco industry e.g. optical, infrared, laser, ultrasound, ultraviolet, Roentgen, gamma, capacitive, microwave and other sensors. The radiation receivers 8', 9', 10', 11' receive or reflect the signals emitted by the corresponding radiation sources 8, 9, 10, 11.

In FIG. 2 flanges 18, 19, 20, 21, 22 formed in the protective member 13 are shown. The flanges 19, 20, 21 project inward the protective member 13 and the flanges 18, 22 delimit the endings of the member 13, all of the flanges defining the compartments 14, 15, 16, 17 (best seen in FIG. 4). The compartments 14, 15, 16, 17 correspond to respective operation zones 8A, 9A, 10A, 11A (best seen in FIG. 3), indicated by dotted lines 25.

The flanges 18, 19, 20, 21, 22 and the rod-like element CR travelling within the protective member 13 delimit a space corresponding to each sensor unit 8-8', 9-9', 10-10', 11-11', each space being located between an internal wall 23 of the protective member 13, a peripheral wall 24 of said rod-like element and two neighboring flanges. Each compartment of the protective member 13 comprises at least one first opening 8B, 9B, 10B, 11B enabling percolation of the radiation emitted and received or reflected by the sensor units 8-8', 9-9', 10-10', 11-11'. As shown in FIG. 2, each opening 8B, 9B, 10B, 11B is located opposite to a corresponding sensor unit.

Due to such configuration of the flanges 18, 19, 20, 21, 22 and to the openings that limit the width of a radiation beam, each operation zone 8A, 9A, 10A, 11A of a respective sensor unit 8-8', 9-9', 10-10', 11-11' is substantially inaccessible to the radiation emitted by the neighboring sensor units. The distance by which the flanges 18, 19, 20, 21, 22 project inward the protective member 13 is adapted to the diameter of the rod-like element. The protective member 13 shown in the figures has a tubular shape, preferably of a circular cross-section; however it may also have a rectangular or polygonal cross-section. Consequently, the compartments may have respectively a cylindrical, cuboid or prismatic shape.

In FIG. 3 the measuring head 4 according to a second embodiment is shown. The figure shows a theoretical situation where the protective member 13 has been removed. In this embodiment the radiation sources 8, 9, 10, 11 and the radiation receivers 8', 9', 10', 11' of each sensor unit are located on opposite sides of the through channel 12. As shown in FIG. 3, with the protective member removed, the radiation emitted by the specific sensor units 8-8', 9-9', 10-10', 11-11' goes beyond their respective operation zones 8A, 9A, 10A, 11A, i.e. the spaces located between the specific radiation sources 8, 9, 10, 11 and their respective radiation receivers 8', 9', 10', 11'.

In FIG. 4 a longitudinal section of the measuring head of FIG. 3 with the protective member 13 present inside. However, in FIG. 4 the rod-like element is not present inside. The flanges 18, 19, 20, 21, 22 formed in the protective member 13 are clearly seen. The flanges 18, 19, 20, 21, 22 project inside the protective member 13 or delimit its endings and define the compartments 14, 15, 16, 17 corresponding respectively to the operation zones 8A, 9A, 10A, 11A. Apart from the first openings 8B, 9B, 10B, 11B, the protective member 13 comprises the opposite second openings 8B', 9B', 10B', 11B' enabling reception of the radiation emitted by the sources 8, 9, 10, 11 by their respective receivers 8', 9', 10', 11'.

In FIG. 4 an exemplary radiation beam is shown, its width having been limited upon passing through the first opening 9B.

FIG. 5 shows the same second embodiment of the measuring head 4 shown in FIGS. 2 and 3, with the protective member 13 present and the rod-like element, i.e. the rod CR travelling within. An exemplary radiation beam emitted by the source 9 is also shown, the beam passing through the first opening 9B, then through the rod CR and finally through the second opening 9B' to the radiation receiver 9'.

The protective member 13 may be made of metal, e.g. stainless steel, and generally of a material radiopaque to the radiation used in the measuring head or of a material suitable for insulating the operation zones of the sensors. The protective member 13 may be screwed or clamped to a frame of a machine or it may be attached by any typical method enabling easy replacement.

The invention claimed is:

1. A protective member for rod-like elements, travelling within a measuring head used in tobacco industry, the measuring head comprising at least two neighboring sensor units configured to take measurements of the parameters of said rod-like elements by measuring radiation emitted and received by said sensor units, the protective member extending through operation zones of the at least two neighboring sensor units, the protective member comprising compartments defined therein, each compartment corresponding to the operation zone of one of the at least two sensor units and each compartment comprising at least one first opening configured to percolate said radiation, wherein the protective member has a generally tubular shape and separate compartments are defined by flanges, each flange delimiting, together with the rod-like elements travelling within the protective member, a space assigned to each sensor unit, said space being located between a peripheral wall of the rod-like element, two neighboring flanges and an internal wall of the protective member, and said space being substantially inaccessible to radiation emitted by the neighboring sensor units, wherein the flanges are spaced axially along the protective member and extend radially inward with respect to the internal wall of the protective member.

2. The protective member according to claim 1, wherein each compartment further comprises at least one second opening configured to percolate said radiation, located opposite to the corresponding first opening, each sensor unit comprising a radiation source located on one side of the protective member and a radiation receiver located on an opposite side of the protective member opposite to the respective radiation source.

3. The protective member according to claim 1, wherein the protective member comprises a material that is radiopaque to the radiation emitted and received by the sensor units, the radiation being selected from a group comprising visible radiation, infrared radiation and ultraviolet radiation.

4. The protective member according to claim 1, wherein the flanges extend radially inwardly from an innermost surface of the internal wall of the protective member.

5. A measuring head for use in tobacco industry, the measuring head comprising:
at least two neighboring sensor units configured to take measurements of parameters of rod-like elements travelling within the measuring head, by measuring radiation emitted and received by the sensor units, and
a protective member for the rod-like elements extending through operation zones of the at least two neighboring sensor units,
the protective member comprising compartments defined in the protective member, each compartment corresponding to an operation zone of one sensor unit and
each compartment comprising at least one first opening configured to percolate said radiation,
wherein the protective member has a generally tubular shape,
wherein each of the compartments in the protective member are defined by flanges, each flange delimiting, together with the rod-like element travelling within the protective member, a space assigned to each sensor unit,
wherein the space is located between the peripheral wall of at least one of the rod-like elements, two neighboring flanges and the internal wall of the protective member, and the space is substantially inaccessible to the radiation emitted by neighboring sensor units, and
wherein the flanges are spaced axially along the protective member and extend radially inward with respect to the internal wall of the protective member.

6. The measuring head according to claim 5, wherein each sensor unit comprises a radiation source and a radiation receiver, both being located on one side of the protective member.

7. The measuring head according to claim 5, wherein each sensor unit comprises a radiation source located on one side of the protective member and a radiation receiver located on an opposite side of the protective member opposite to the respective radiation source, each compartment of the protective member further comprising at least one second opening configured to percolate said radiation, located opposite to a corresponding first opening.

8. The measuring head according to claim 5, wherein the protective member of the measuring head comprises a material radiopaque to the radiation emitted and received by the sensor units, the radiation being selected from a group comprising visible radiation, infrared radiation and ultraviolet radiation.

9. The measuring head according to claim 5, wherein the flanges extend radially inwardly from an innermost surface of the internal wall of the protective member.

* * * * *